United States Patent
Sudai

(10) Patent No.: US 6,168,624 B1
(45) Date of Patent: Jan. 2, 2001

(54) APPARATUS AND METHODS FOR REVASCULARIZATION AND PERFUSION

(76) Inventor: Amnon Sudai, 10 Yona Angel St., Ramat Golda, Haifa (IL)

(*) Notice: Under 35 U.S.C. 154(b), the term of this patent shall be extended for 0 days.

(21) Appl. No.: 09/180,886

(22) PCT Filed: May 20, 1997

(86) PCT No.: PCT/IL97/00162

§ 371 Date: Nov. 16, 1998

§ 102(e) Date: Nov. 16, 1998

(87) PCT Pub. No.: WO97/44071

PCT Pub. Date: Nov. 27, 1997

(30) Foreign Application Priority Data

May 21, 1996 (IL) .......................................... 118352

(51) Int. Cl.$^7$ ................................................ A61M 1/10
(52) U.S. Cl. ...................... 623/3.21; 623/3.28; 623/904; 600/16
(58) Field of Search ............................ 623/3, 3.21, 3.26, 623/3.28, 902, 904; 600/16

(56) References Cited

U.S. PATENT DOCUMENTS

| 5,409,019 | 4/1995 | Wilk . |
| 5,429,144 | 7/1995 | Wilk . |
| 5,531,789 | * 7/1996 | Yamasaki et al. ...................... 623/12 |
| 5,755,682 | 5/1998 | Knudson et al. . |
| 5,810,836 | * 9/1998 | Hussein et al. ........................ 623/12 |

* cited by examiner

*Primary Examiner*—Paul B. Prebilic
(74) *Attorney, Agent, or Firm*—Mark M. Friedman

(57) ABSTRACT

The invention is practiced by introducing a catheter (10) into the left ventricle of the heart. Deployment of an intraventricular pump assembly (12) from the end of catheter (10) is carried out by pushing holding device (24) in direction of the arrow (26). The tubes (20) of the intraventricular pump assembly (16) swing outward to protrude from hub (18). The first intraventricular pump (16) has a resilient bulb (30) attached to the hub (18). The tubes (20) are then self-anchored the myocardium such that they can act to inject blood into the myocardial wall from the ventricle.

17 Claims, 11 Drawing Sheets

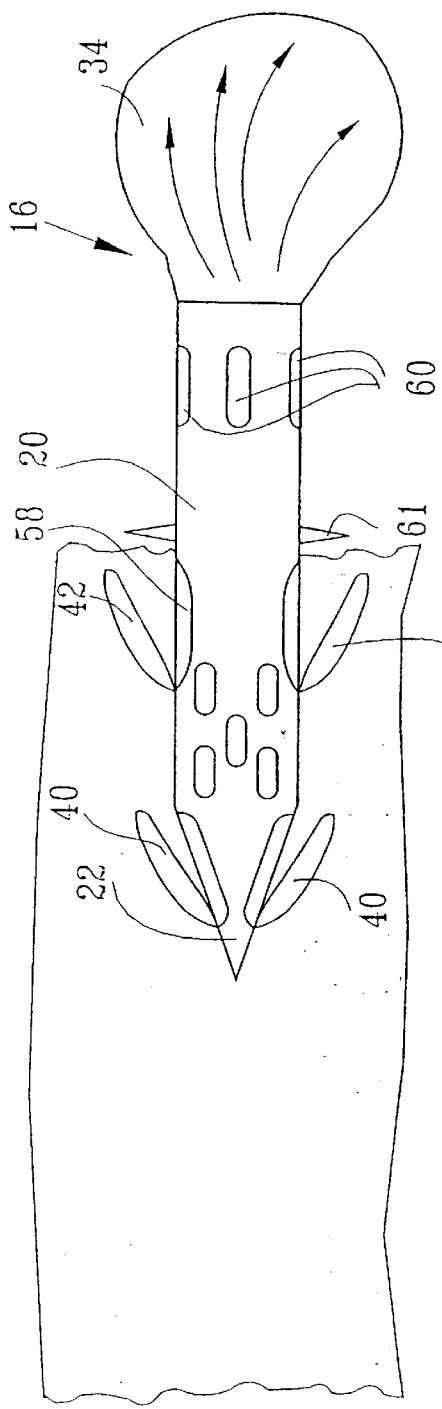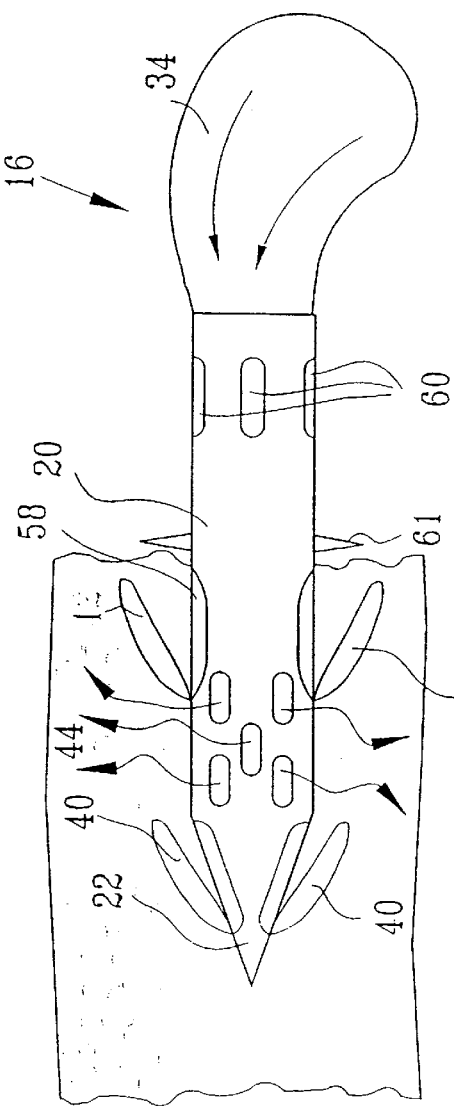
FIG. 8A
FIG. 8B

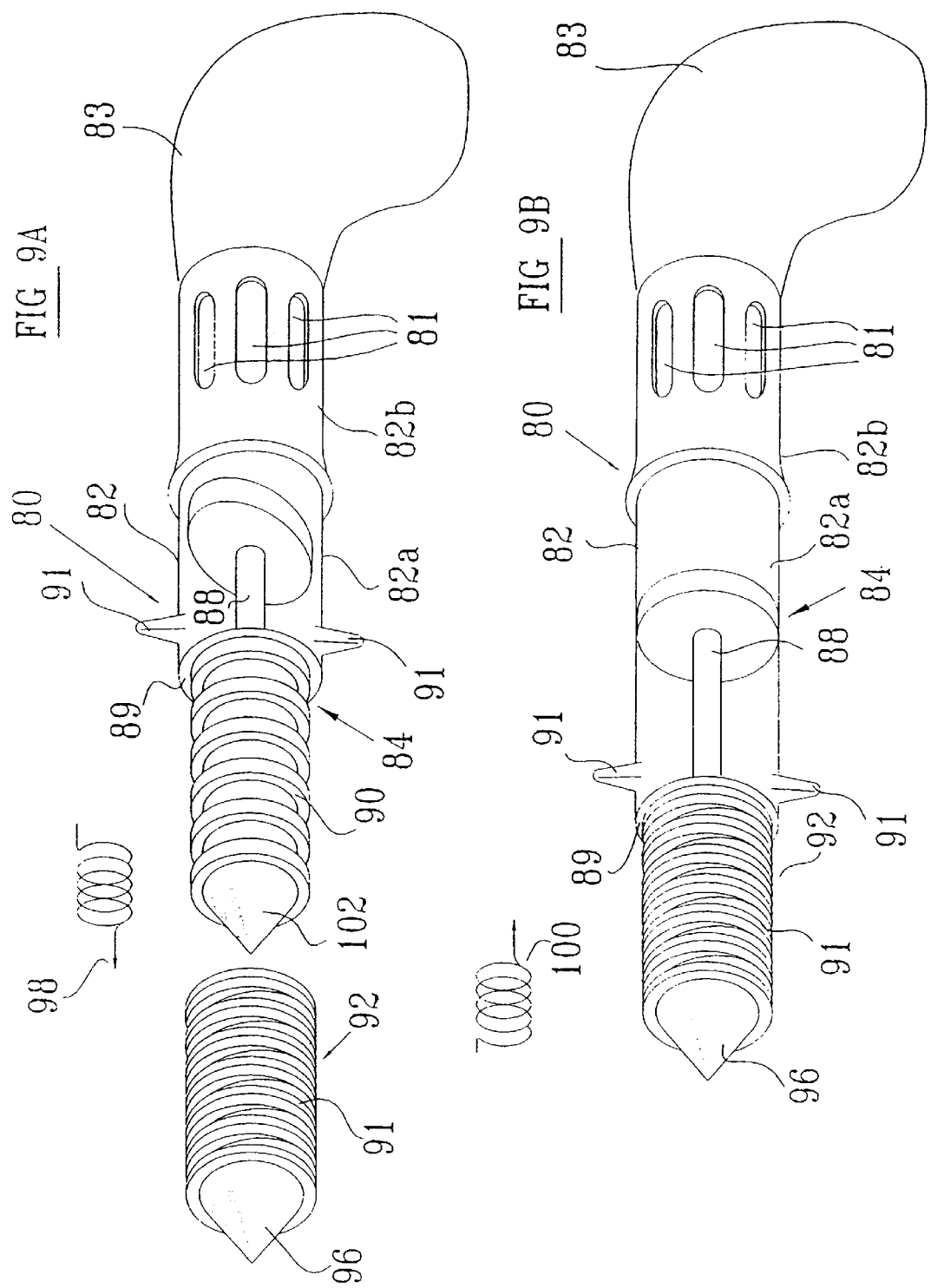

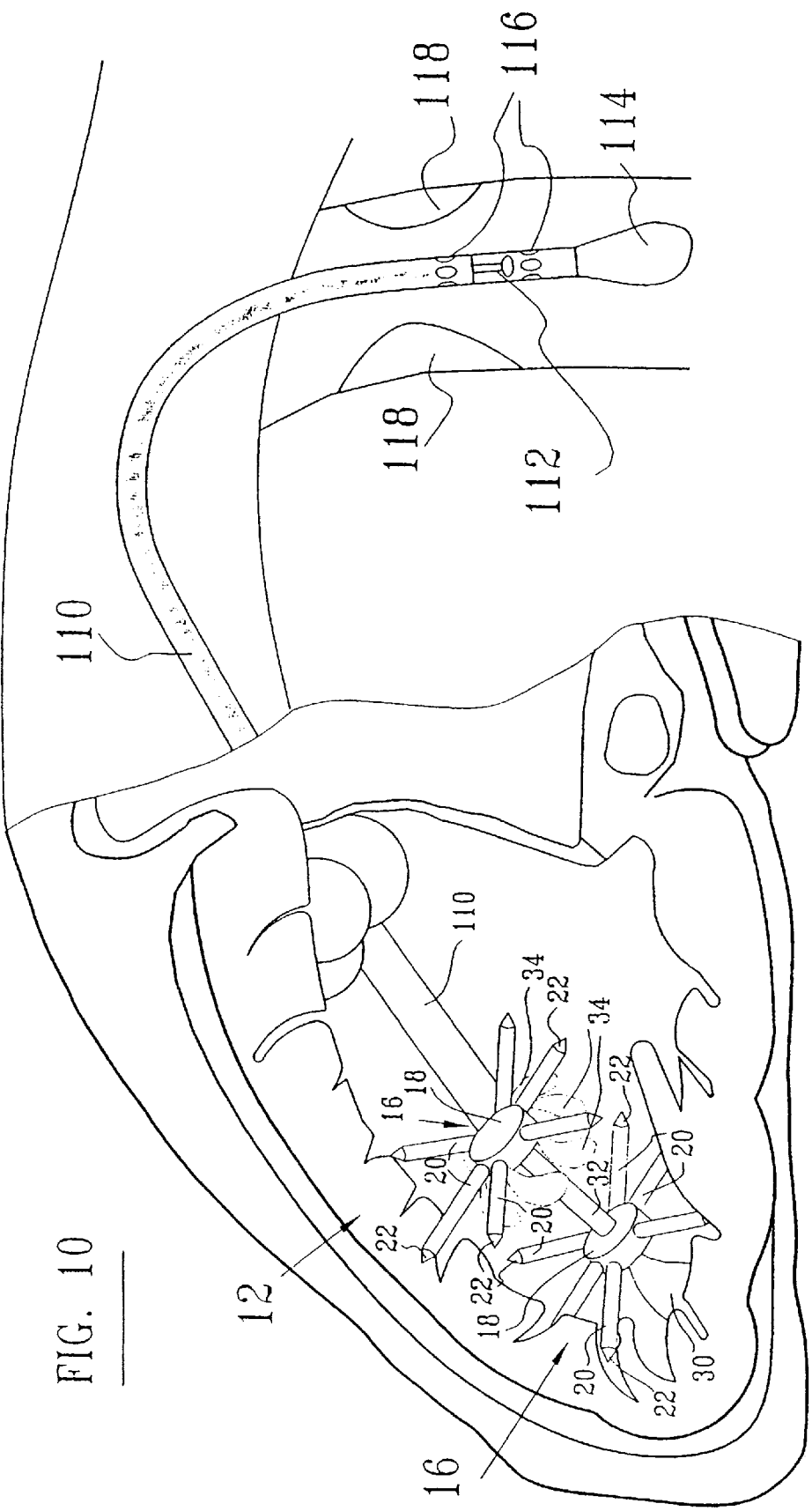

APPARATUS AND METHODS FOR REVASCULARIZATION AND PERFUSION

FIELD AND BACKGROUND OF THE INVENTION

The present invention relates to cardiology generally and particularly to methods and apparatus for intramyocardial and intraventricular revascularization and perfusion.

In a normal heart, the myocardium is supplied with blood via the coronary arteries during diastole. In certain heart diseases or malfunctions, particularly involving arteriosclerotic coronary arteries, the myocardial tissue does not receive an adequate supply of blood, and may become dormant or "hibernate" and eventually become necrotic. Myocardial damage due to coronary disease is the largest cause of death in the Western world.

Coronary bypass surgery and coronary angioplasty are well known techniques for combating problems due to arteriosclerotic coronary arteries. However, bypass and angioplasty techniques for most patients are not long term solutions. Recently a technique called transmyocardial laser revascularization (TLR) has been introduced. A series of holes are drilled through the myocardial wall. When the procedure is finished, what remains are blind holes in the myocardial wall which are open inwards to the intraventricular cavity. During the pumping action of the heart, blood flows directly into the blind holes and hopefully nourishes the myocardial tissue, thereby compensating for the malfunctioning coronary arteries.

TLR is gaining more and more use because it appears to be suitable for a greater population of heart disease patients, and may be implemented as a last resort when other solutions have failed or cannot be used.

Nevertheless, there are several disadvantages to TLR. It is a long surgical procedure with general anesthesia. The position of the holes to be drilled may be difficult to plan, and in some places it may be impossible to drill. Extreme caution must be exercised to avoid damage to the heart muscle or other body tissues and organs, and to prevent disturbances in the heartbeat. Furthermore, in a normal heart, blood is pumped to the myocardium during diastole, whereas in TLR, it is not yet clear whether blood is pumped into the myocardial tissue during systole or diastole. In addition, the blind holes may tend to collapse or close up with time.

SUMMARY OF THE INVENTION

The present invention seeks to provide an improved methods and apparatus for revascularization and perfusion which are intramyocardial and intraventricular.

In accordance with a preferred embodiment of the present invention, an intraventricular pump or pump assembly is introduced into the left ventricle by a catheter. The pump preferably includes a valve disposed inside a tube.

During systole, the valve may either be inactive or may divert flow of blood into a reservoir. During diastole, the valve opens and blood is pumped into the tube from the reservoir, and further into the myocardial wall. Thus, the myocardial tissue is correctly and efficiently nourished with blood during diastole.

Preferably a plurality of such pumps are anchored in predetermined strategic locations in the ventricular wall, so as to provide an optimal supply of blood to the myocardial tissue.

The procedure of the present invention substantially overcomes the disadvantages of the prior art. The procedure is non-surgical, does not require general anesthesia and may be quickly performed. The procedure may be employed when immediate myocardial revascularization is warranted and other procedures of the art cannot be used.

There is thus provided in accordance with a preferred embodiment of the present invention, a method for intraventricular revascularization and perfusion of a myocardium, including the steps of introducing at least one pump into a ventricle of a heart, the at least one pump including an inlet for flow of fluid therein and an outlet for flow of fluid therefrom, and attaching the at least one pump to the myocardium so that the outlet is in fluid communication therewith, such that while the heart beats, the at least one pump draws blood from the ventricle via the inlet and pumps blood into the myocardium via the outlet, thereby causing revascularization and perfusion of the myocardium.

In accordance with a preferred embodiment of the present invention, the at least one pump draws blood from the ventricle during systole and pumps blood into the myocardium during diastole. Preferably a catheter is used to introduce the at least one pump into the ventricle. Preferably the method further includes substantially spatially fixing a portion of the at least one pump inside the ventricle.

In accordance with a preferred embodiment of the present invention, the method includes using a reservoir in fluid communication with the at least one pump for drawing blood thereinto during systole and for pumping blood therefrom during diastole.

Additionally in accordance with a preferred embodiment of the present invention, the method includes introducing a plurality of the pumps into the ventricle, wherein the pumps share a common reservoir for drawing blood thereinto during systole and for pumping blood therefrom during diastole. Preferably the method includes substantially spatially commonly fixing a portion of the pumps inside the ventricle.

In accordance with a preferred embodiment of the present invention, the method includes fluidly connecting one end of a bypass tube to the at least one pump and passing another end of the bypass tube out of the ventricle, the other end of the bypass tube being in fluid communication with an extraventricular blood vessel, wherein pumping of the at least one pump causes blood to be pumped through the bypass tube to the blood vessel.

There is also provided in accordance with a preferred embodiment of the present invention, an intraventricular pump for intraventricular revascularization and perfusion of a myocardium, including a tube of such size which permits insertion thereof into a ventricle of a heart by means of a catheter, a tip of the tube being insertable into the myocardium, the tube being formed with at least one aperture for flow of blood therethrough, such that during systole blood flows through the at least one aperture into the tube. The pump preferably includes a valve disposed inside the tube, such that during diastole the valve opens, thereby allowing blood to be pumped through the tube into the myocardium, thereby causing revascularization and perfusion thereof.

In accordance with a preferred embodiment of the present invention there is also provided a reservoir in fluid communication with the tube, wherein the valve permits drawing blood into the reservoir during systole and wherein during diastole, the valve opens to permit the pump to pump blood from the reservoir into the myocardium.

Additionally in accordance with a preferred embodiment of the present invention, there is provided at least one anchoring member for anchoring the tube to the myocardium.

Further in accordance with a preferred embodiment of the present invention, there is provided fixing apparatus for substantially spatially fixing an outer surface of the tube in the ventricle.

There is also provided in accordance with a preferred embodiment of the present invention, an intraventricular pumping assembly for intraventricular revascularization and perfusion of a myocardium, including a plurality of pumps, each pump including a tube of such size which permits insertion thereof into a ventricle of a heart by means of a catheter, a tip of the tube being insertable into the myocardium, the tube being formed with at least one aperture for flow of blood therethrough. preferably, the tube includes a valve disposed inside the tube, such that during diastole the valve opens, thereby permitting blood to be pumped through the tube into the myocardium, thereby causing revascularization and perfusion thereof.

In accordance with a preferred embodiment of the present invention, the assembly includes a reservoir in fluid communication with at least one of the tubes, for drawing blood thereinto during systole and for pumping blood therefrom during diastole. The reservoir may be common to at least some of the tubes.

Preferably the pumps are commonly substantially spatially fixed inside the ventricle. Furthermore, the intraventricular pump assembly preferably includes an anchoring member for anchoring each tube to the myocardium.

There is also provided in accordance with a preferred embodiment of the present invention, an intraventricular stent of such size which permits insertion thereof into a ventricle by means of a catheter, the stent including a sleeve portion which is insertable and fixable in a myocardium. Preferably the sleeve portion includes a coil. The stent may have a pointed tip which is insertable into the myocardium.

BRIEF DESCRIPTION OF THE DRAWINGS

The present invention will be understood and appreciated more fully from the following detailed description, taken in conjunction with the drawings in which:

FIGS. 8A and 8B are simplified illustrations of an intraventricular pump, constructed and operative in accordance with another preferred embodiment of the present invention, during systole and diastole, respectively, wherein blood is pumped into the myocardium during diastole;

FIGS. 9A and 9B are simplified, partially sectional illustrations of an intraventricular pump, constructed and operative in accordance with yet another preferred embodiment of the present invention; and FIG. 10 is a simplified, partially sectional illustration of a bypass tube fluidly connected to the intraventricular pump of FIG. 5, in accordance with a preferred embodiment of the present invention.

DESCRIPTION OF THE PREFERRED EMBODIMENTS

Figure 1:
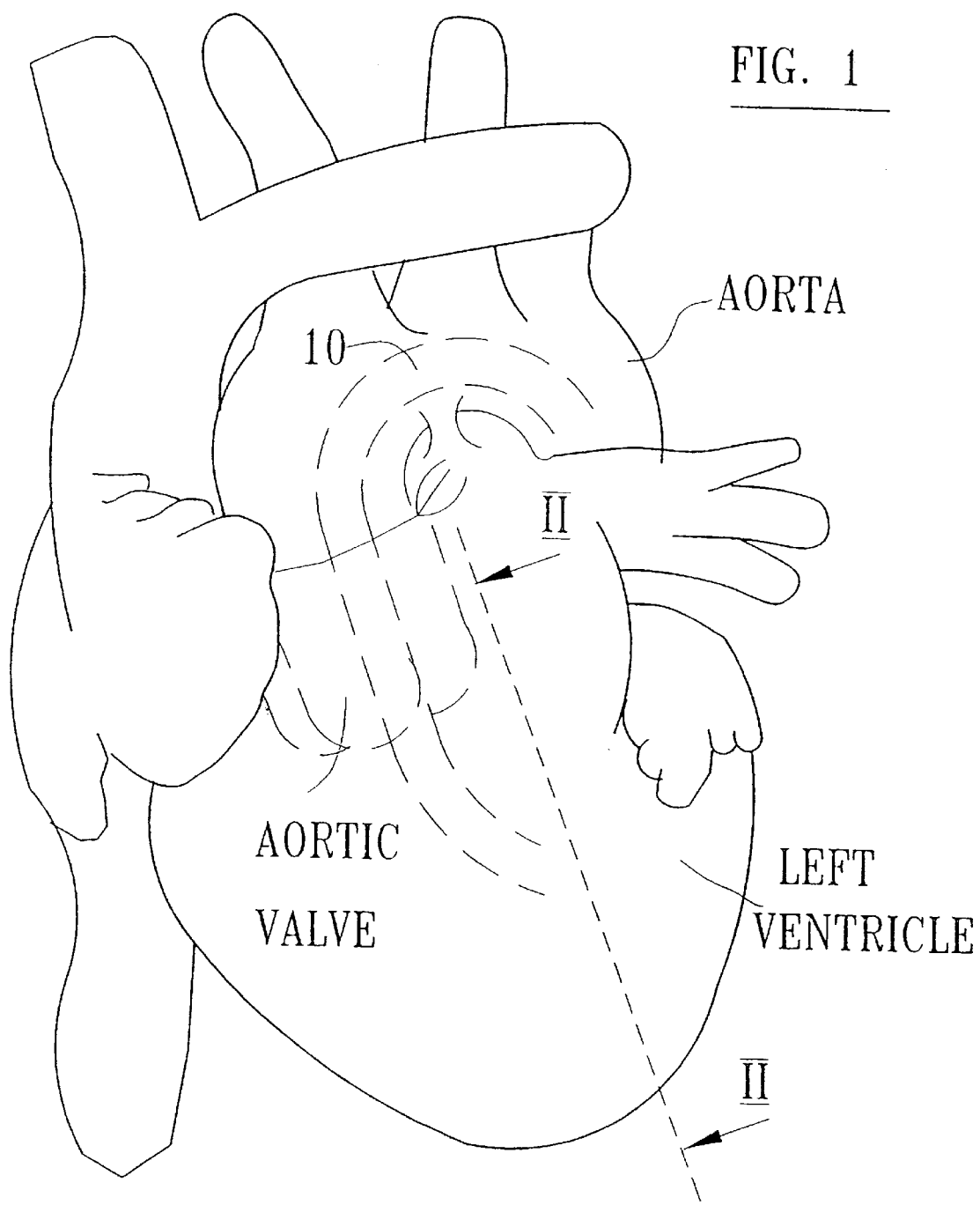
FIG. 1 is a simplified pictorial illustration of a catheter being introduced into the left ventricle of the heart through the aorta, in accordance with a preferred embodiment of the present invention.
Figure 2:
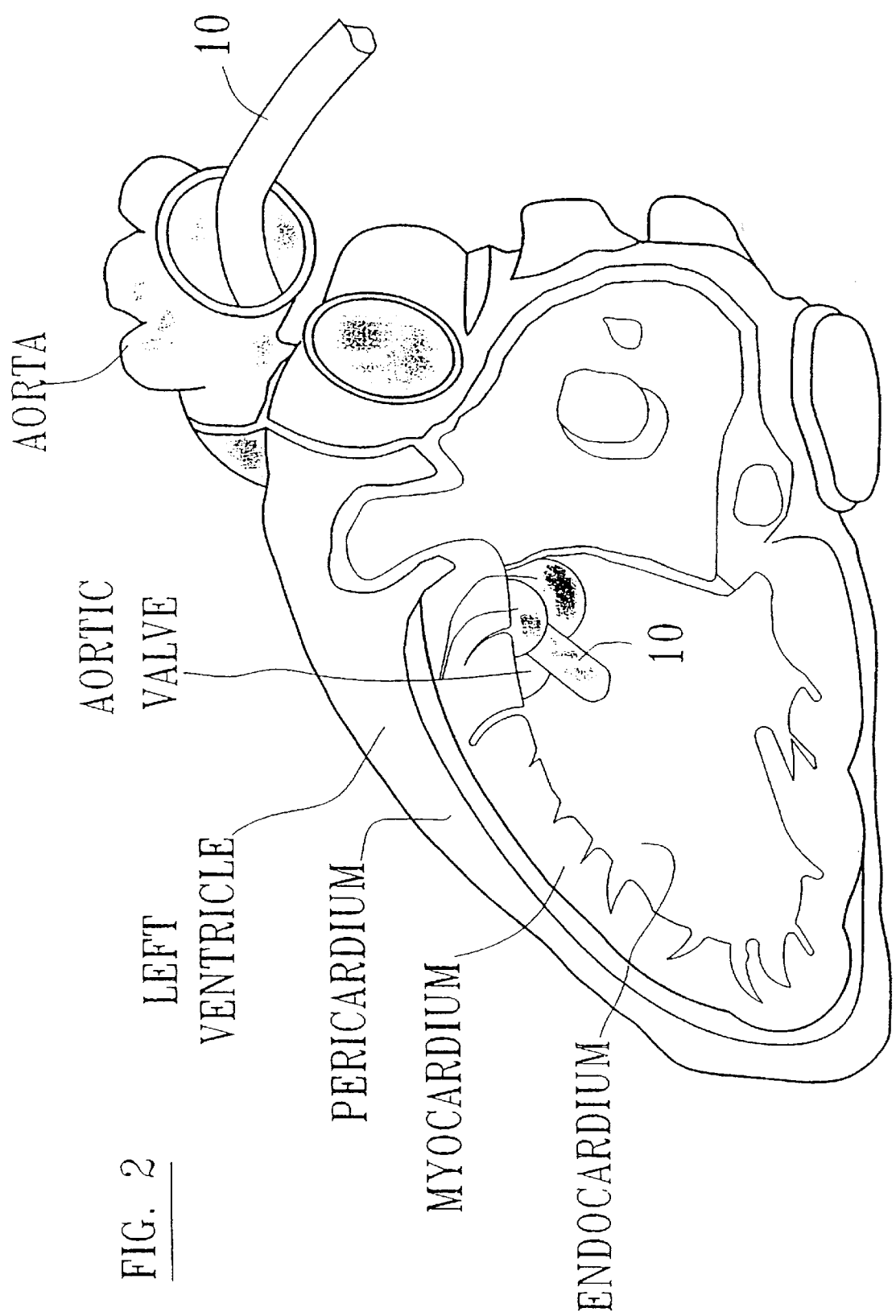
FIG. 2 is a simplified sectional illustration of the catheter being introduced into the left ventricle, taken along lines II—II in FIG. 1.

Reference is now made to FIGS. 1 and 2 which illustrate a catheter 10 being introduced into the left ventricle of a heart through the aorta and aortic valve, in accordance with a preferred embodiment of the present invention. Catheter 10 is preferably introduced via the femoral artery using conventional techniques.

Figure 3:
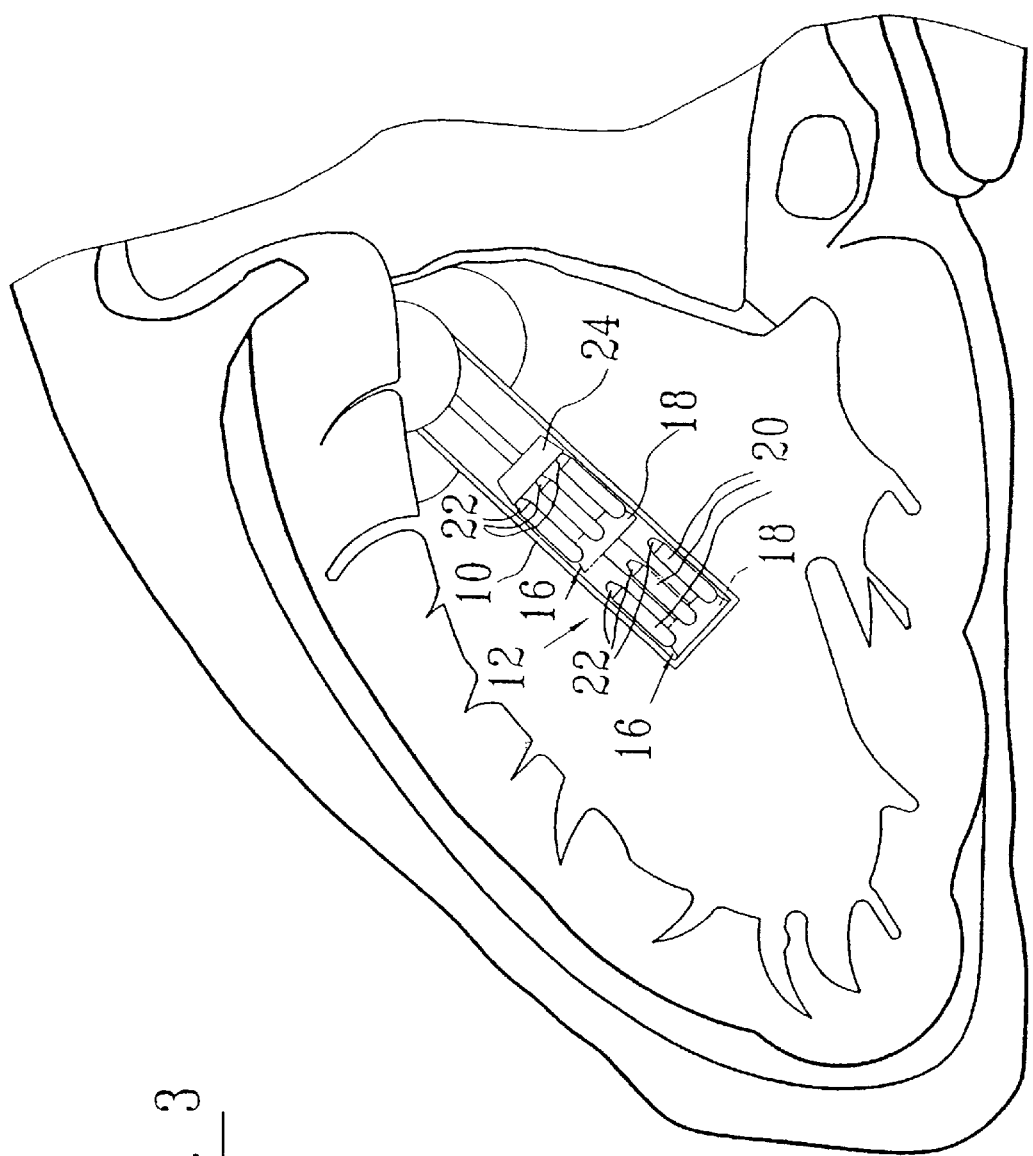
FIG. 3 is a simplified, partially sectional illustration of an intraventricular pump assembly, constructed and operative in accordance with a preferred embodiment of the present invention, introduced by the catheter into the left ventricle.

Reference is now made to FIG. 3 which illustrates an intraventricular pump assembly 12, constructed and operative in accordance with a preferred embodiment of the present invention, preferably disposed in a distal end 14 of catheter 10. Intraventricular pump assembly 12 preferably includes one or more intraventricular pumps 16 disposed one after the other in distal end 14 of catheter 10. Each intraventricular pump 16 preferably includes a hub 18 to which are rotatably attached a plurality of tubes 20 with pointed tips 22. Tubes 20 are preferably spring loaded with respect to hub 18 so that when intraventricular pump 16 exits catheter 10, tubes 20 may swing radially outwards and protrude from hub 18, As shown in FIG. 3, as long as intraventricular pump 16 remains inside catheter 10, tubes 20 are held within the confines of catheter 10.

Intraventricular pumps 16 are preferably releasably attached to a holding device 24 inside catheter 10. Holding device 24 may be a conventional holding device used in catheters for introducing and releasing instruments or substances in the body.

Figure 4:
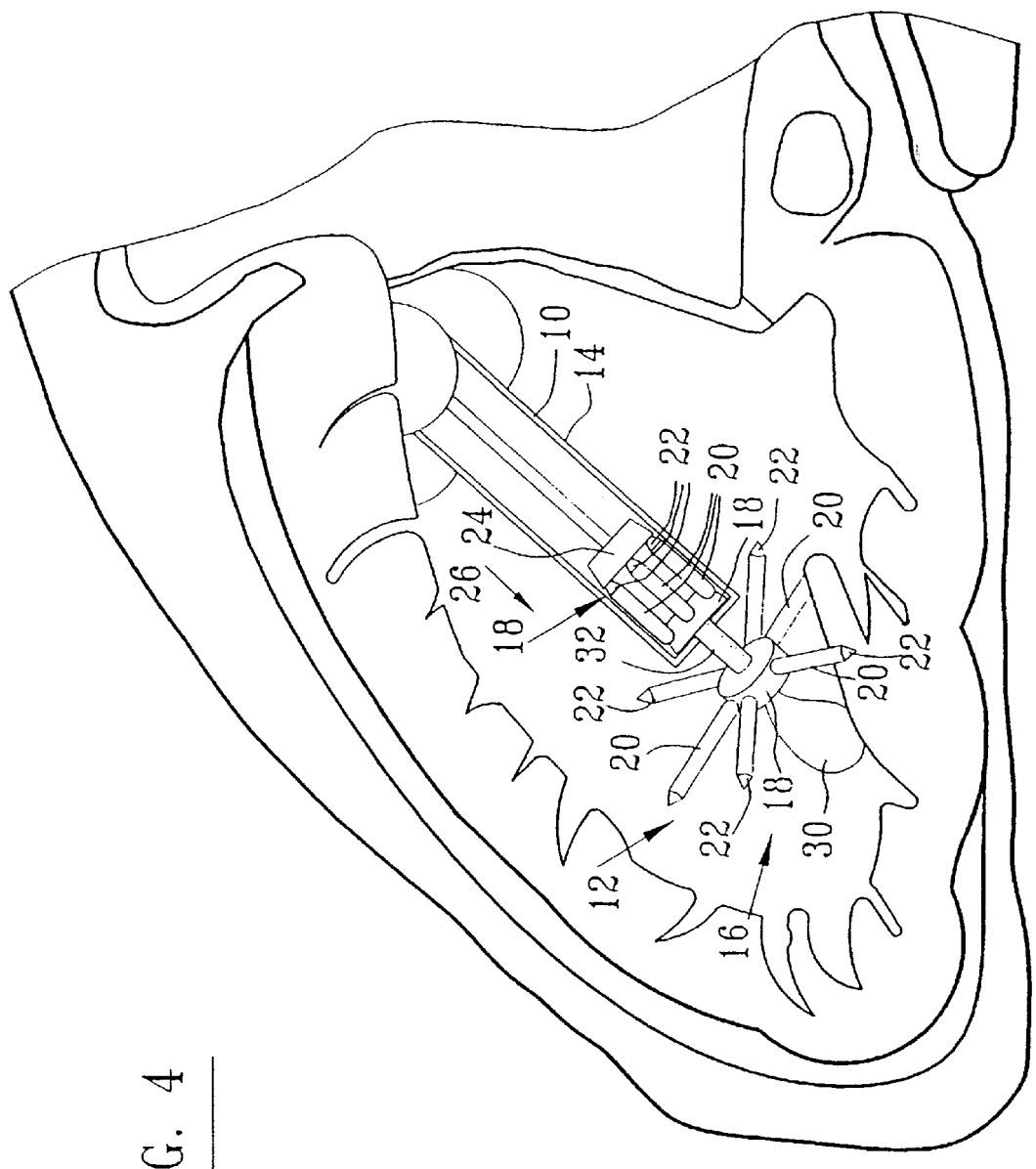
FIGS. 4 and 5 are simplified, partially sectional illustrations of progressive deployment of the intraventricular pump assembly from the catheter.

Reference is now made to FIG. 4 which illustrates initial deployment of intraventricular pump assembly 12 from catheter 10. By pushing holding device 24 generally in the direction of an arrow 26, a first intraventricular pump 16 is pushed out of catheter 10. As soon as the first intraventricular pump 16 fully exits catheter 10. The tubes 20 swing radially outwards and protrude from hub 18. It is seen that the first intraventricular pump 16 may include a reservoir, such as a resilient bulb 30 attached to hub 18. Preferably all of the tubes 20 are in common fluid communication with bulb 30. Preferably a shaft 32 connects the hubs 18 of the two intraventricular pumps 16. Hubs 18 may be expendable or may be constructed in different sizes in accordance with their location in the left ventricle or the size of the ventricle.

Figure 5:
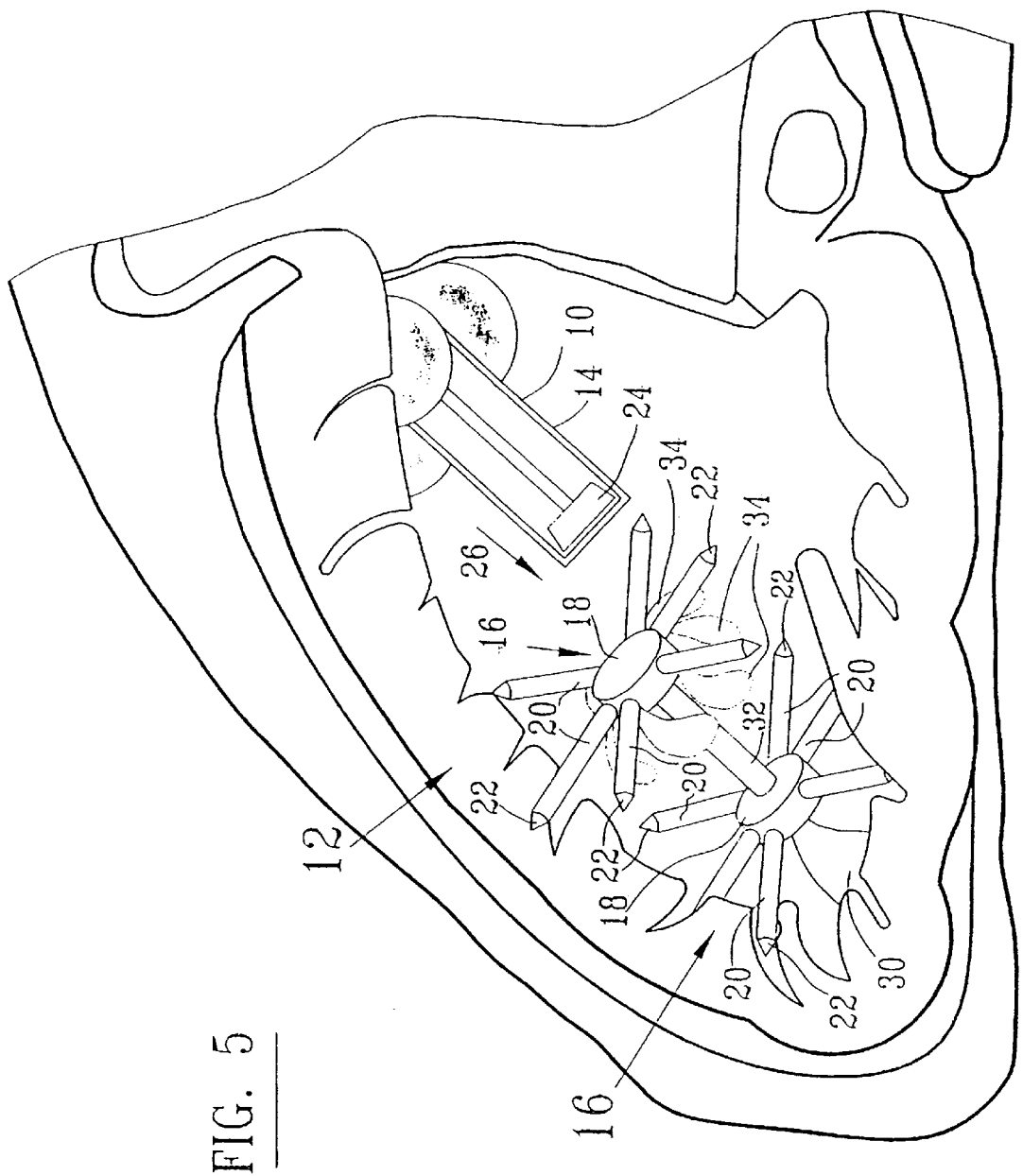

Reference is now made to FIG. 5 which illustrates further deployment of intraventricular pump assembly 12 from catheter 10. By further pushing holding device 24 generally in the direction of arrow 26, a second intraventricular pump 16 is pushed out of catheter 10. As soon as the second intraventricular pump 16 fully exits catheter 10, the tubes 20 swing radially outwards and protrude from hub 18. It is seen that the second intraventricular pump 16 may include a plurality of reservoirs, such as resilient bulbs 34, each attached to a corresponding tube 20. In this arrangement, the tubes 20 are preferably not in common fluid communication with each other.

After having deployed all the pumps 16 of intraventricular pump assembly 12, holding device 24 is preferably released from the assembly 12 and catheter 10, along with holding device 24, may be retracted from the heart and body.

As will now be described with reference to FIGS. 6A–6D, the movement of the myocardial muscle during systole of the left ventricle causes pointed tips 22 of the tubes 20 to pierce the endocardium and myocardium and become embedded in the myocardium. Thus, in accordance with the techniques of the present invention, the intraventricular pump assembly 12 is introduced into the left ventricle by the catheter 10 and becomes self-anchored to the myocardium by the systolic action of the left ventricle. Intraventricular pump assembly 12 may be extracted from the patient's body at any time.

Reference is now made to FIGS. 6A–6D which illustrate one of the intraventricular pumps 16, constructed and operative in accordance with a preferred embodiment of the present invention, penetrating the myocardium and being anchored therein. FIGS. 6A–6D in particular illustrate one of the tubes 20 of the second intraventricular pump 16 with its bulb 34, although it is appreciated that the description which follows is equally applicable to any of the tubes 20 of the first intraventricular pump 16 with their common bulb 30. Hub 18 is not shown for clarity.

Figure 6A:
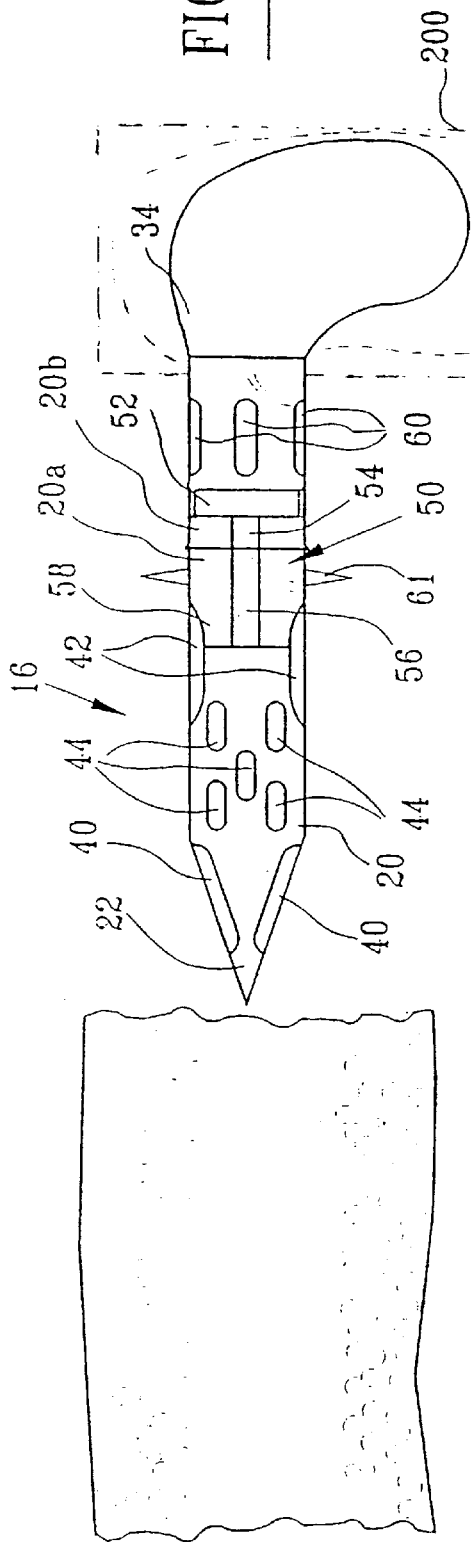
FIGS. 6A–6D are simplified, partially sectional illustrations of an intraventricular pump of the intraventricular pump assembly, constructed and operative in accordance with a preferred embodiment of the present invention, penetrating the myocardium and being anchored therein.

As seen in FIG. 6A, tube 20 preferably includes a first 40 and a second 42 sets of deployable tabs which are preferably hingedly attached to tube 20. The first set of tabs 40 is preferably located near pointed tip 22, whereas the second set of tabs 42 is preferably located on the body of tube 20 a small distance, such as 1–2 cm, proximally away from the first set of tabs 40. A plurality of holes 44 is preferably formed on tube 20 between both sets of tabs 40 and 42.

In accordance with a preferred embodiment of the present invention, tube 20 preferably includes two cylindrical elements 20a and 20b such that cylindrical element 20a is telescopically slidable within cylindrical element 20b. According to a preferred embodiment, cylindrical element 20b is preferably connected to a container 200 attached to hub 18 (not shown in the figures), the container for accommodating bulb 34. Container 200 is preferably rigid, and includes a chamber 202 filled with a fluid of a predetermined pressure. Further, a valve 50 is disposed inside tube 20, valve 50 being preferably attached to cylindrical element 20a and proximal to both sets of tabs 40 and 42. Valve 50 preferably includes a piston head 52 pivotally attached to a shaft 54 which telescopically slides in a generally cylindrical sheath 56 fixedly attached to cylindrical element 20a by means of a ring 58. Ring 58 is preferably constructed with apertures (not shown) which allow passage of fluid therethrough inside tube 20.

Tube 20 is further preferably provided with a plurality of apertures 60 formed thereon, generally proximally away from the location of piston head 52 shown in FIG. 6A. Apertures 60 may permit passage of fluid therethrough in and out of tube 20. Preferably, apertures 60 include unidirectional valves for selectively allowing passage of fluid into tube 20 and preventing passage of fluid out of tube 20.

In FIG. 6A, tip 22 has just contacted the myocardial wall, and the left ventricle is in diastole.

Figure 6B:
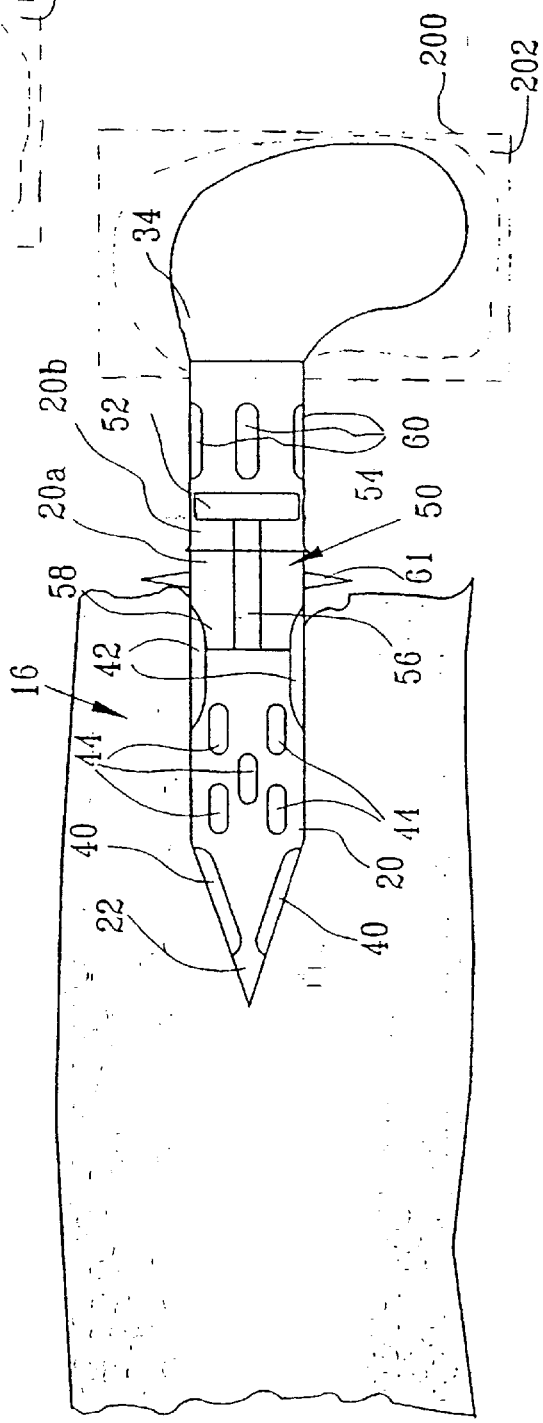

In FIG. 6B, the left ventricle is in systole and the movement of the myocardial muscle causes tip 22 to pierce the endocardium and enter the myocardium. Tube 20 is preferably provided with one or more stops 61 which substantially prevent overpenetration of tube 20 into the myocardium.

Figure 6C:
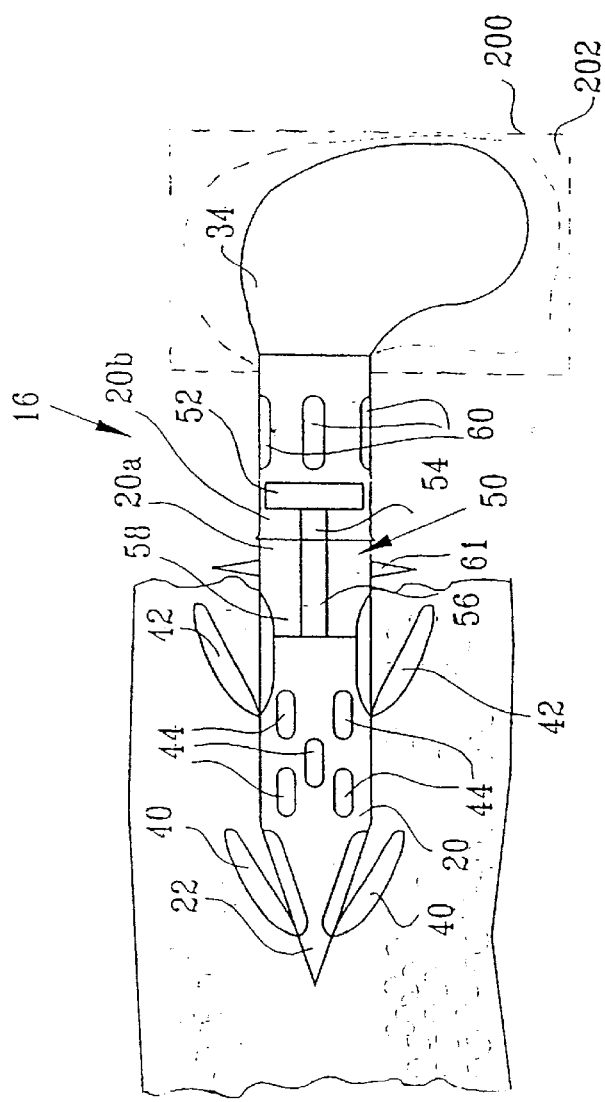

In FIG. 6C, the left ventricle is again in diastole and tabs 40 and 42 dig into the myocardial tissue and become embedded therein.

Figure 6D:
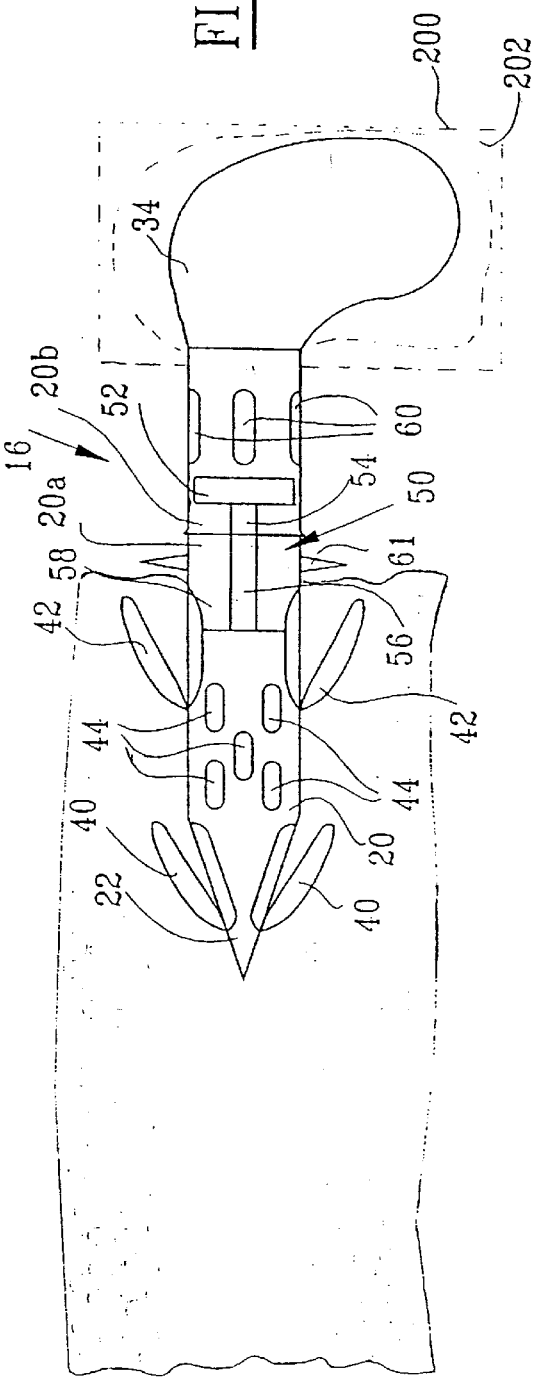

In FIG. 6D, the left ventricle is again in systole. It is seen that tube 20 is now substantially firmly anchored in the myocardium.

It is noted that for the sake of clarity, any pumping action associated with tube 20 has not been illustrated in FIGS. 6A–6D. The pumping action will now be described.

Figure 7A:
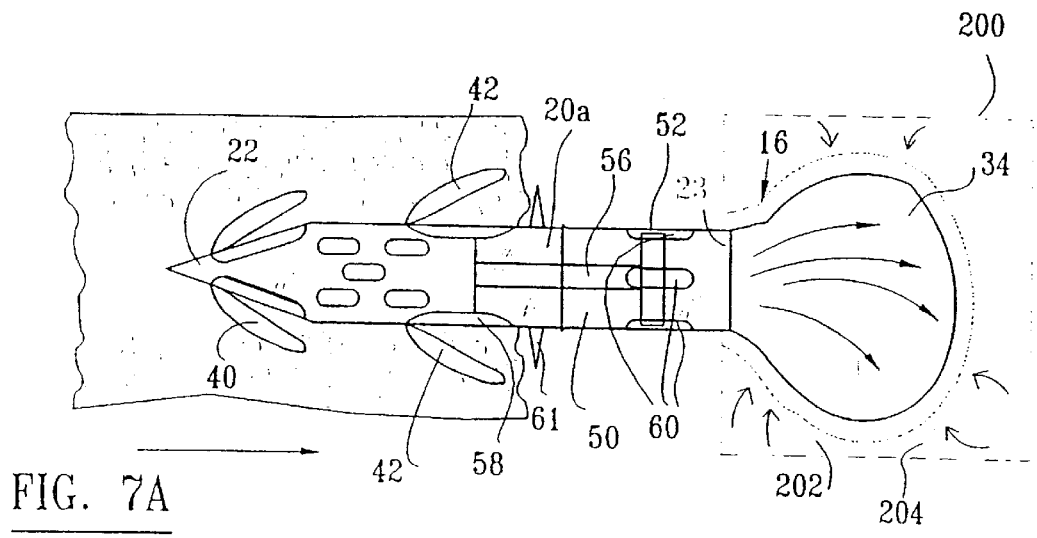
FIGS. 7A, 7B and 7C are simplified, partially sectional illustrations of the pumping action of the intraventricular pump during systole and diastole.
Figure 7B:
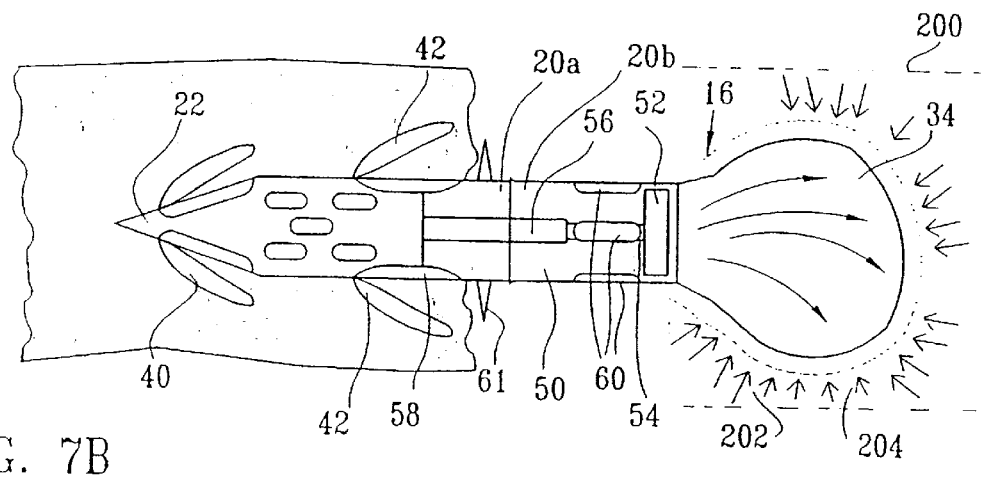
Figure 7C:
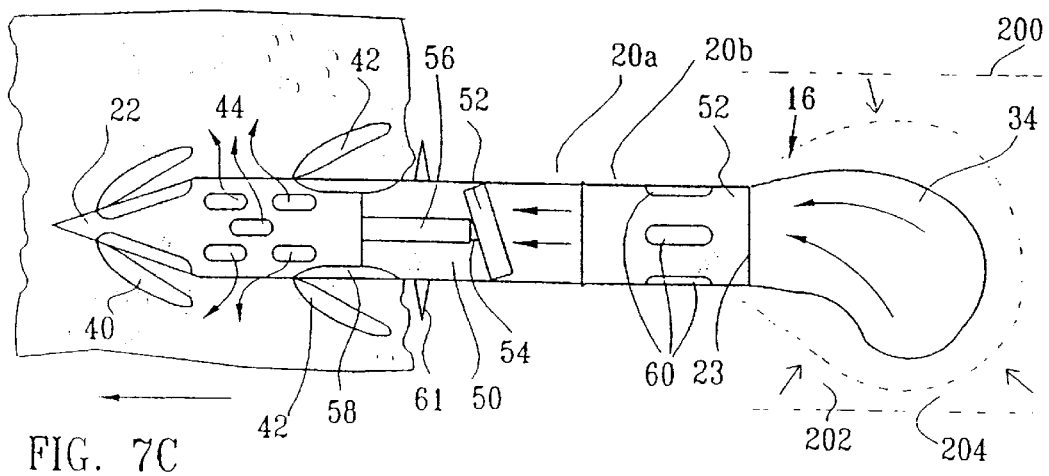

Reference is now made to FIGS. 7A, 7B and 7C which illustrate the pumping action of intraventricular pump 16. In FIG. 7A, the left ventricle is in systole. The movement of the myocardium during systole (illustrated by an arrow) causes cylindrical element 20a to telescopically move within cylindrical element 20b towards container 200, thereby causing piston head 52 to compress the blood within tube 20 into bulb 34. The systolic force causes piston head 52 to remain substantially perpendicular with respect to shaft 54 and cylindrical sheath 56.

It is noted that piston head 52 is free to move inside cylindrical element 20b because once all of the cylindrical elements 20a of the intraventricular pumps 16 are fully anchored in the myocardium, cylindrical elements 20b are substantially mutually fixed in the ventricular space. Thus, while cylindrical element 20b is substantially held fixed, piston head 52 is free to move with respect thereto.

In addition, the systolic pressure built within the left ventricle causes blood to penetrate through apertures 60 into tube 20 and bulb 34. Since shaft 54 is telescopically slidable within cylindrical sheath 56, such blood causes piston head 52 to further move towards bulb 34, as shown in FIG. 7b, thereby further compressing the blood within bulb 34. The pressure built within bulb 34 depends on the pressure of the fluid within chamber 202, and is predetermined.

In FIG. 7C, the left ventricle is in diastole. The movement of the myocardium during diastole (illustrated by an arrow) causes cylindrical element 20a to telescopically move within cylindrical element 20b away from container 200. The blood compressed within bulb 34 during systole is now forced by the positive pressure built within container 200 towards the myocardium. Since apertures 60 include unidirectional valves, flow of blood out of tube 20 is prevented. As shown in FIG. 7C, the blood forced towards the myocardium presses piston head 52 and therefore causes shaft 54 to slide back into cylindrical sheath 56. Further, the retractive force of the diastole causes piston head 52 to rotate with respect to shaft 54, thereby allowing blood which accumulated in bulb 34 during systole to flow through tube 20 past piston head 52 and into the myocardium via apertures 44, This flow of blood causes revascularization and perfusion of the myocardium. The timing and intensity of blood injection into the myocardium may be determined by the pressure of fluid within chamber 202.

According to another configuration (not shown), shaft 54 is not telescopically slidable within cylindrical sheath 56, but rather fixed to ring 58. Further, piston head 52 may be fixedly mounted on shaft 54 and substantially perpendicular thereto.

According to another embodiment (not shown), pump 16 does not include a container 202 and a bulb 34. Rather, piston head 52 includes a spring which can be forced against proximal end 23 of tube 20 during systole. In this embodiment proximal end 23 is connected to hub 18. Thus, during systole piston head 52 is forced towards the myocardium by means of the spring. Alternatively, the spring may be placed on proximal end 23. When using such an embodiment, the timing and intensity of blood injection into the myocardium may be determined by the spring constant.

Thus, two main mechanisms are used for driving the intraventricular pump: (a) conversion of kinetic energy provided by movement of the myocardium during systole into potential energy stored within an elastic bulb or a spring, wherein during diastole such potential energy is converted into kinetic energy of blood within the pump; and (b) conversion of potential energy provided by pressure build-up within the ventricle during systole into potential energy stored within an elastic bulb or spring, wherein during systole such potential energy is converted into kinetic energy of blood within the pump.

Another preferred embodiment which uses the latter mechanism only is shown in FIGS. 8A and 8B. According to such embodiment tube 20 does not include cylindrical elements 20a and 20b. Further, valve 50 is not included.

In FIG. 8A the left ventricle is in systole. The systolic pressure built within the ventricle causes blood to penetrate through apertures 60 into tube 20 and bulb 34 which is received within container 200 (not shown). The pressure built within bulb 34 depends on the pressure of the fluid within chamber 202 (not shown), and is preferably predetermined.

In FIG. 8B the left ventricle is in diastole. The blood compressed within bulb 34 during systole is now forced towards the myocardium. The timing and intensity of blood injection into the myocardium may be determined by the pressure of the fluid within chamber 202 (not shown).

According to another embodiment bulb 34 may be connected to a plurality of pumps 16 and may be accommodated within a central container placed within the ventricular space. In such embodiment hub 18 is not used.

According to another preferred embodiment (not shown), at least one of pumps 16 extends through the myocardium and reaches the terminal epicardial coronary arteries, or alternatively the bifurcation of the coronary arteries so as to directly pump blood thereto.

Bulb 34 may be coated with biologically active materials such as anti-ahrrithmogenic drugs, tissue proliferation inducers, muscle relaxation drugs and anti-thrombogenic factors. Alternatively, the biologically active materials may be accommodated within capsules contained within bulb 34. Further, bulb 34 may include imaging agents.

Reference is now made to FIGS. 9A and 9B which illustrate an intraventricular pump 80, constructed and operative in accordance with yet another preferred embodiment of the present invention.

Intraventricular pump 80 preferably includes a tube 82 having a cylindrical element 82a telescopically slidable within a cylindrical element 82b and in which is disposed a valve 84. Tube 82 preferably has apertures 81 formed therein and may be in fluid communication with a reservoir 83, in a similar manner as described hereinabove with respect to intraventricular pump 16. Valve 84 preferably includes a piston head 86 which may be pivotally or fixedly mounted on a shaft 88. Shaft 88 is preferably fixedly attached to a relatively thin "pancake" bearing 89 which is rotatably attached to a threaded barrel 90 (FIG. 9A). Preferably one or more stops 91 are attached to tube 82 proximally with respect to bearing 89.

Intraventricular pump 80 preferably further includes a stent 92. Stent 92 preferably includes a sleeve portion, such as a coil 94 with a pointed tip 96. Threaded barrel 90 and coil 94 are preferably configured such that threaded barrel 90 can easily thread into coil 94, generally in the direction indicated by an arrow 98, and threaded barrel 90 can easily thread out of coil 94, generally in the direction indicated by an arrow 100. Threaded barrel 90 preferably includes a pointed tip 102 (FIG. 9A) which may cut tissue as threaded barrel 90 moves in and out of coil 94, thereby helping to maintain a clear passage of blood into the myocardium for revascularization and perfusion thereof.

It is noted that threaded barrel 90 is shown detached from coil 94 in FIG. 9A only for purposes of clarity. In operation, threaded barrel preferably remains in threaded engagement with coil 94 at all times. FIG. 9B shows valve 84 fully engaged with coil 94 and threaded barrel 90 is not visible.

Intraventricular pump 80 preferably operates in a manner similar to that described hereinabove with respect to FIGS. 7A and 7B for intraventricular pump 16. Cylindrical element 82b of intraventricular pump 80 is also preferably substantially spatially fixed in a manner similar to that described hereinabove with respect to FIGS. 7A and 7B for intraventricular pump 16.

The intraventricular pumps or pump assemblies of the present invention may be used to pump blood out of the heart as well. Reference is now made to FIG. 10 which illustrates a bypass tube 110 fluidly connected to one of the tubes 20 of the intraventricular pump assembly 12 illustrated in FIG. 5, in accordance with a preferred embodiment of the present invention. Bypass tube 110 is preferably introduced by the catheter 10 (not shown in FIG. 10) when introducing the intraventricular pump assembly 12 into the left ventricle.

The other end of bypass tube 110 preferably exits the ventricle through the aortic valve and is preferably fluidly connected to a valve 112 and a reservoir 114. Valve 112 is preferably a one-way type of valve and may be the same type of valve used in intraventricular pumps 16 or 80, described hereinabove with respect to FIGS. 7A, 7B, 9A and 9B. A plurality of apertures 116 are preferably formed on bypass tube 110 distally and/or proximally of valve 112.

Bypass tube 110 may be used to supply blood to an artery, such as the left anterior descending (LAD) artery, wherein a constriction 118 constricts flow of blood therethrough. As seen in FIG. 10, bypass tube 110 is preferably passed through constriction 118 such that valve 112, reservoir 114 and apertures 116 are downstream of constriction 118. During diastole valve 112 is preferably open, and blood is pumped through bypass tube 110 and flows past constriction 118 and valve 112, the blood then being collected in reservoir 114 and/or exiting through apertures 116.

During systole valve 112 is preferably closed, and blood collected in reservoir 114 flows back out to the LAD artery through apertures 116 located between reservoir 114 and valve 112. Thus, bypass tube 110 provides a method for bypassing constrictions in arteries and providing flow of blood to such arteries.

An apparatus according to the present invention may be electrically connected to an electrophysiological device such as a pace maker or any other electrical sensing and/or pacing device so as to provide timely based electromechanical perfusion.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

While the invention has been described with respect to a limited number of embodiments, it will be appreciated that many variations, modifications and other applications of the invention may be made.

What is claimed is:

1. A method for intraventricular revascularization and perfusion of a myocardium, comprising the steps of:

(a) introducing at least one pump into a ventricle of a heart, said at least one pump comprising an inlet for flow of fluid therein and an outlet for flow of fluid therefrom;

(b) attaching said at least one pump to the myocardium so that said outlet is in fluid communication therewith; and (c) using a reservoir in fluid communication with said at least one pump for drawing blood thereinto during systole and for pumping blood therefrom during diastole, such that while the heart beats, said at least one pump draws blood from the ventricle via said inlet and pumps blood into the myocardium via said outlet.

2. A method for intraventricular revascularization and perfusion of a myocardium, comprising the steps of:

(a) introducing at least one pump into a ventricle of a heart, said at least one pump comprising an inlet for flow of fluid therein and an outlet for flow of fluid therefrom;

(b) attaching said at least one pump to the myocardium so that said outlet is in fluid communication therewith, and (c) introducing a plurality of said pumps into said ventricle, wherein said pumps share a common reservoir for drawing blood thereinto during systole and for pumping blood therefrom during diastole, such that while the heart beats, said at least one pump draws blood from the ventricle via said inlet and pumps blood into the myocardium via said outlet.

3. The method of claim 2, further comprising substantially spatially commonly fixing a portion of said pumps inside the ventricle.

4. A method for intraventricular revascularization and perfusion of a myocardium, comprising the steps of:

(a) introducing at least one pump into a ventricle of a heart, said at least one pump comprising an inlet for flow of fluid therein and an outlet for flow of fluid therefrom;

(b) attaching said at least one pump to the myocardium so that said outlet is in fluid communication therewith; and (c) fluidly connecting one end of a bypass tube to said at least one pump and passing another end of said bypass tube out of said ventricle, said other end of said bypass tube being in fluid communication with an extraventricular blood vessel, wherein pumping of said at least one pump causes blood to be pumped through said bypass tube to said blood vessel;

such that while the heart beats, said at least one pump draws blood from the ventricle via said inlet and pumps blood into the myocardium via said outlet.

5. An intraventricular pump for intraventricular revascularization and perfusion of a myocardium, comprising:

(a) a tube of such size which permits insertion thereof into a ventricle of a heart by means of a catheter, a tip of said tube being insertable into the myocardium, said tube being formed with at least one aperture for flow of blood therethrough; and (b) a valve disposed inside said tube, wherein during diastole said valve opens causing blood to be pumped through said tube into the myocardium, further comprising a reservoir in fluid communication with said tube, wherein said valve permits drawing blood into said reservoir during systole and wherein during diastole, said valve opens to permit said pump to pump blood from said reservoir into the myocardium.

6. An intraventricular pump for intraventricular revascularization and perfusion of a myocardium, comprising:

(a) a tube of such size which permits insertion thereof into a ventricle of a heart by means of a catheter, a tip of said tube being insertable into the myocardium, said tube being formed with at least one aperture for flow of blood therethrough; and (b) a valve disposed inside said tube, wherein during diastole said valve opens causing blood to be pumped through said tube into the myocardium;

further comprising fixing apparatus for substantially spatially fixing an outer surface of said tube in said ventricle;

wherein said tube further includes:

a first cylindrical element for anchoring to the myocardium and a second cylindrical element fixed to said fixing apparatus, said first cylindrical element being slidably movable within said second cylindrical element; and a piston element connected to said first cylindrical element, such that during systole said first cylindrical element slides within said second cylindrical element, thereby causing said piston element to force blood towards said fixing apparatus.

7. The pump of claim 6, further comprising a reservoir in fluid communication with said second cylindrical element for drawing blood thereinto during systole and pumping blood therefrom during diastole.

8. The pump of claim 6, further comprising a spring connected to at least one of said piston element and said second cylindrical element.

9. The pump of claim 6, wherein said piston element includes a piston head pivotally connected to a shaft.

10. The pump of claim 9, wherein said piston element is slidably movable within a cylindrical sheath connected to said first cylindrical element.

11. An intraventricular pump for intraventricular revascularization and perfusion of a myocardium, comprising:

(a) a tube of such size which permits insertion thereof into a ventricle of a heart by means of a catheter, a tip of said tube being insertable into the myocardium, said tube being formed at least one aperture for flow of blood therethrough; and (b) a valve disposed inside said tube, wherein during diastole said valve opens causing blood to be pumped through said tube into the myocardium;

wherein said pump is electrically connected to an electrophysiological device so as to provide timely based electromechanical perfusion.

12. An intraventricular pump for intraventricular revascularization and perfusion of a myocardium, comprising:

a tube of such size which permits insertion thereof into a ventricle of a heart by means of a catheter, a tip of said tube being insertable into the myocardium, said tube being formed with at least one aperture for flow of blood therethrough, such that during systole blood flows through said at least one aperture from the ventricle into said tube, and during diastole blood flows through said tube into the myocardium;

further comprising a reservoir in fluid communication with said tube for drawing blood thereinto during systole and pumping blood therefrom during diastole.

13. The intraventricular pump of claim 12, wherein said reservoir includes biologically active materials.

14. The intraventricular pump of claim 12, further comprising a container for accommodating said reservoir so as to generate a predetermined pressure within said reservoir during systole.

15. An intraventricular pumping assembly for intraventricular revascularization and perfusion of a myocardium, comprising:

a plurality of pumps, each of said pumps comprising:

a tube of such size which permits insertion thereof into a ventricle of a heart by means of a catheter, a tip of said tube being insertable into the myocardium, said tube being formed with at least one aperture for flow of blood therethrough, such that during systole blood flows through said at least one aperture from the ventricle into said tube, and during diastole blood flows through said tube into the myocardium;

further comprising a reservoir in fluid communication with at least one of said tubes, for drawing blood thereinto during systole and for pumping blood therefrom during diastole.

16. The pumping assembly of claim 15, wherein said reservoir is common to at least some of said tubes.

17. A method of cardiovascular treatment comprising the steps of:

(a) introducing at least one pump into a ventricle of a heart, said at least one pump comprising an inlet for flow of fluid therein and an outlet for flow of fluid therefrom, and (b) inserting said at least one pump through the myocardium into an artery so that said outlet is in fluid communication with the artery, such that while the heart beats, said at least one pump draws blood from the ventricle via said inlet and pumps blood into the artery via said outlet;

further comprising introducing a plurality of said pumps into the ventricle, wherein said pumps share a common reservoir for drawing blood thereinto during systole and for pumping blood therefrom during diastole.

* * * * *